(12) United States Patent
Smilde et al.

(10) Patent No.: US 9,134,256 B2
(45) Date of Patent: Sep. 15, 2015

(54) METROLOGY METHOD AND APPARATUS, LITHOGRAPHIC SYSTEM AND DEVICE MANUFACTURING METHOD

(71) Applicant: ASML Netherlands B.V., Veldhoven (NL)

(72) Inventors: Hendrik Jan Hidde Smilde, Veldhoven (NL); Omer Abubaker Omer Adam, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 188 days.

(21) Appl. No.: 13/799,673

(22) Filed: Mar. 13, 2013

(65) Prior Publication Data

US 2013/0258310 A1      Oct. 3, 2013

Related U.S. Application Data

(60) Provisional application No. 61/616,398, filed on Mar. 27, 2012.

(51) Int. Cl.
*G03B 27/54* (2006.01)
*G03B 27/32* (2006.01)
(Continued)

(52) U.S. Cl.
CPC .......... *G01N 21/956* (2013.01); *G03F 7/70633* (2013.01); *G03F 7/70683* (2013.01); *G03F 9/7019* (2013.01); *Y10T 428/24802* (2015.01)

(58) Field of Classification Search
CPC ......................... G03F 7/70616; G03F 7/70633
USPC .......................................... 355/52, 53, 55, 67
See application file for complete search history.

(56) References Cited

U.S. PATENT DOCUMENTS 5,757,507 A * 5/1998 Ausschnitt et al. ........... 356/401
7,277,172 B2   10/2007 Kandel et al.
(Continued)

FOREIGN PATENT DOCUMENTS

WO   WO 2009/078708 A1   6/2009
WO   WO 2009/106279 A1   9/2009
WO   WO 2011/012624 A1   2/2011

OTHER PUBLICATIONS

International Search Report directed to related International Patent Application No. PCT/EP2013/054504, mailed Sep. 18, 2013; 4 pages.

*Primary Examiner* — Hung Henry Nguyen
(74) *Attorney, Agent, or Firm* — Sterne, Kessler, Goldstein & Fox P.L.L.C.

(57) ABSTRACT

A lithographic process is used to form a plurality of target structures (T) on a substrate (W). Each target structure comprises overlaid gratings each having a specific overlay bias. Asymmetry (A) of each grating, measured by scatterometry, includes contributions due to (i) the overlay bias, (ii) an overlay error (OV) in the lithographic process and (iii) bottom grating asymmetry within the overlaid gratings. Asymmetry measurements are obtained for three or more target structures having three or more different values of overlay bias (e.g., −d, 0, +d). Knowing the three different overlay bias values and a theoretical curve relationship between overlay error and asymmetry, overlay error (OV) can be calculated while correcting the effect of bottom grating asymmetry. Bias schemes with three and four different biases are disclosed as examples. Gratings with different directions and biases can be interleaved in a composite target structure.

17 Claims, 6 Drawing Sheets

(51) Int. Cl.
*G01N 21/956* (2006.01)
*G03F 9/00* (2006.01)
*G03F 7/20* (2006.01)

(56) References Cited

U.S. PATENT DOCUMENTS

| | | | |
|---|---|---|---|
| 7,532,305 | B2 | 5/2009 | Den Boef et al. |
| 8,411,287 | B2 * | 4/2013 | Smilde et al. ............... 356/620 |
| 2004/0169861 | A1 | 9/2004 | Mieher et al. |
| 2005/0012928 | A1 | 1/2005 | Sezginer et al. |
| 2006/0274310 | A1 | 12/2006 | Kandel et al. |
| 2010/0284008 | A1 | 11/2010 | Coene et al. |
| 2011/0001978 | A1 | 1/2011 | Smilde et al. |
| 2011/0027704 | A1 | 2/2011 | Cramer et al. |
| 2011/0043791 | A1 | 2/2011 | Smilde et al. |
| 2012/0044470 | A1 | 2/2012 | Smilde et al. |
| 2012/0113404 | A1 | 5/2012 | Hsu et al. |

* cited by examiner

METROLOGY METHOD AND APPARATUS, LITHOGRAPHIC SYSTEM AND DEVICE MANUFACTURING METHOD

BACKGROUND

1. Field of the Invention

The present invention relates to methods and apparatus for metrology usable, for example, in the manufacture of devices by lithographic techniques and to methods of manufacturing devices using lithographic techniques.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

The targets used by conventional scatterometers are relatively large, e.g., 40 µm by 40 µm, gratings and the measurement beam generates a spot that is smaller than the grating (i.e., the grating is underfilled). This simplifies mathematical reconstruction of the target as it can be regarded as infinite. However, in order to reduce the size of the targets, e.g., to 10 µm by 10 µm or less, e.g., so they can be positioned in amongst product features, rather than in the scribe lane, metrology has been proposed in which the grating is made smaller than the measurement spot (i.e., the grating is overfilled). Typically such targets are measured using dark field scatterometry in which the zeroth order of diffraction (corresponding to a specular reflection) is blocked, and only higher orders processed. Diffraction-based overlay using dark-field detection of the diffraction orders enables overlay measurements on smaller targets. These targets can be smaller than the illumination spot and may be surrounded by product structures on a wafer. Multiple targets can be measured in one image.

In the known metrology technique, overlay measurement results are obtained by measuring the target twice under certain conditions, while either rotating the target or changing the illumination mode or imaging mode to obtain separately the −1st and the +1st diffraction order intensities. Comparing these intensities for a given grating provides a measurement of asymmetry in the grating, and asymmetry in an overlay grating can be used as an indicator of overlay error.

Although the known dark-field image-based overlay measurements are fast and computationally very simple (once calibrated), they rely on an assumption that overlay is the only cause of asymmetry in the target structure. Any other asymmetry in the stack, such as asymmetry of features within one or both of the overlaid gratings, also causes an asymmetry in the 1st orders. This asymmetry which is not related to the overlay clearly perturbs the overlay measurement, giving an inaccurate overlay result. Asymmetry in the bottom grating of the overlay grating is a common form of feature asymmetry. It may original for example in wafer processing steps such as chemical-mechanical polishing (CMP), performed after the bottom grating was originally formed.

Accordingly at this time the skilled person has to choose between, on the one hand, a simple and fast measurement process that gives overlay measurements but is subject to inaccuracies when other causes of asymmetry are present, and on the other hand more traditional techniques that are computationally intensive and typically require several measurements of large, underfilled gratings to avoid the pupil image is polluted with signal from the environment of the overlay grating, which hampers the reconstruction on this.

SUMMARY

Therefore, it is desired to distinguish the contributions to target structure asymmetry that are caused by overlay and other effects in a more direct and simple way.

It is desirable to provide a method and apparatus for overlay metrology using target structures, in which throughput and accuracy can be improved over prior published techniques. Furthermore, although the invention is not limited to this, it would be of great advantage, if this could be applied to small target structures that can be read out with the dark-field image-based technique.

A first embodiment of the present invention provides a method of measuring a parameter of a lithographic process, the method comprising using the lithographic process to form a plurality of target structures on a substrate, each target structure comprising overlaid periodic structures and each having a specific overlay bias, illuminating the targets and detecting radiation scattered by each target structure to obtain for that target structure a measurement representing an overall asymmetry that includes contributions due to (i) the overlay bias, (ii) an overlay error in the lithographic process and (iii) feature asymmetry within one or more of the periodic structures, using the overall asymmetry measurements for three or more target structures having three or more different values of overlay bias to calculate a measurement of overlay error, the calculation being performed using knowledge of the three different overlay bias values and an assumed non-linear relationship between overlay error and target asymmetry, thereby to exclude the contribution due to feature asymmetry.

A second embodiment of the present invention provides an inspection apparatus for measuring a parameter of a lithographic process, the apparatus comprising a support for a substrate having a plurality of target structures thereon, each target structure comprising overlaid periodic structures and each having a specific overlay bias, an optical system for illuminating the targets and detecting radiation scattered by each target structure to obtain for that target structure a measurement representing an overall asymmetry that includes contributions due to (i) the overlay bias, (ii) an overlay error in the lithographic process and (iii) feature asymmetry within one or more of the periodic structures, a processor arranged to use the overall asymmetry measurements for three or more target structures having three or more different values of overlay bias to calculate a measurement of overlay error, the calculation being performed using knowledge of the three different overlay bias values and an assumed non-linear relationship between overlay error and target asymmetry, thereby to exclude the contribution due to feature asymmetry.

The assumed non-linear relationship may be for example a sinusoidal function, or optionally a combination of sinusoidal functions related harmonically to one another. The calculation may be performed with the assumption that the contribution due to feature asymmetry is constant for all values of overlay.

In some embodiments of the invention, three different overlay bias values are used. In other embodiments, four different overlay bias values are used. The different overlay bias values span a range greater than 5%, 10%, optionally greater than 15% or 20%, of a pitch of the periodic structures.

In certain embodiments, asymmetry measurements for the three or more target structures are performed in parallel by capturing radiation scattered from the different target structures on different portions of an image sensor.

A third embodiment of the present invention provides a substrate for use in a method or apparatus according to the invention as set forth above. The substrate having a plurality of target structures formed thereon by a lithographic process, each target structure comprising overlaid periodic structures and each having a specific overlay bias, including target structures with periodicity in a first direction having three or more different values of overlay bias and target structures with periodicity in a second direction having three or more different values of overlay bias. The target structures are arranged in a composite target structure in an alternating pattern so that the structures having periodicity in the first direction are separated by structures having periodicity in the second direction.

In one embodiment, six rectangular target structures having three different biases in each of two different directions are arranged in a 2×3 array to form the composite target structure. In another embodiment, eight rectangular target structures having four different biases in each of two different directions are arranged in a 2×4 array to form the composite target structure. The invention is not limited to examples having three or four different biases.

Another embodiment of the present invention provides a substrate for use in a method or apparatus according to the invention as set forth above substrate. The substrate having a plurality of target structures formed thereon by a lithographic process, each target structure comprising overlaid periodic structures and each having a specific overlay bias, including target structures having three or more different values of overlay bias. The overlay bias values span a range greater than 10%, optionally greater than 15% or 20%, of a pitch of the periodic structures. Providing a wide range of bias values helps in the calculation to distinguish the curved form of the assumed relationship, particularly if the asymmetry measurements are subject to a significant degree of noise.

A still further embodiment of the present invention provides a pair of patterning devices for use in forming a substrate according to any aspect of the invention as set forth above, the patterning devices together being adapted for use in forming the target structures with at least three overlay biases.

Another embodiment of the present invention provides a computer program product comprising machine-readable instructions for causing a processor to perform the processing step (c) of a method according to the invention as set forth above.

A still further embodiment of the present invention provides a lithographic system comprising a lithographic apparatus arranged to transfer a sequence of patterns from patterning devices onto a substrate in an overlying manner, and an inspection apparatus according to the invention as set forth above. The lithographic apparatus is arranged to use the calculated overlay values from the inspection apparatus in applying the sequence of patterns to further substrates.

A method of manufacturing devices such that a sequence of device patterns is applied to a series of substrates in an overlying manner using a lithographic process, the method including inspecting at least one periodic structure formed as part of or beside the device patterns on at least one of the substrates using an inspection method according to the invention as set forth above, and controlling the lithographic process for later substrates in accordance with the calculated overlay error.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

The accompanying drawings, which are incorporated herein and form part of the specification, illustrate the present invention and, together with the description, further serve to explain the principles of the invention and to enable a person skilled in the relevant art(s) to make and use the invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
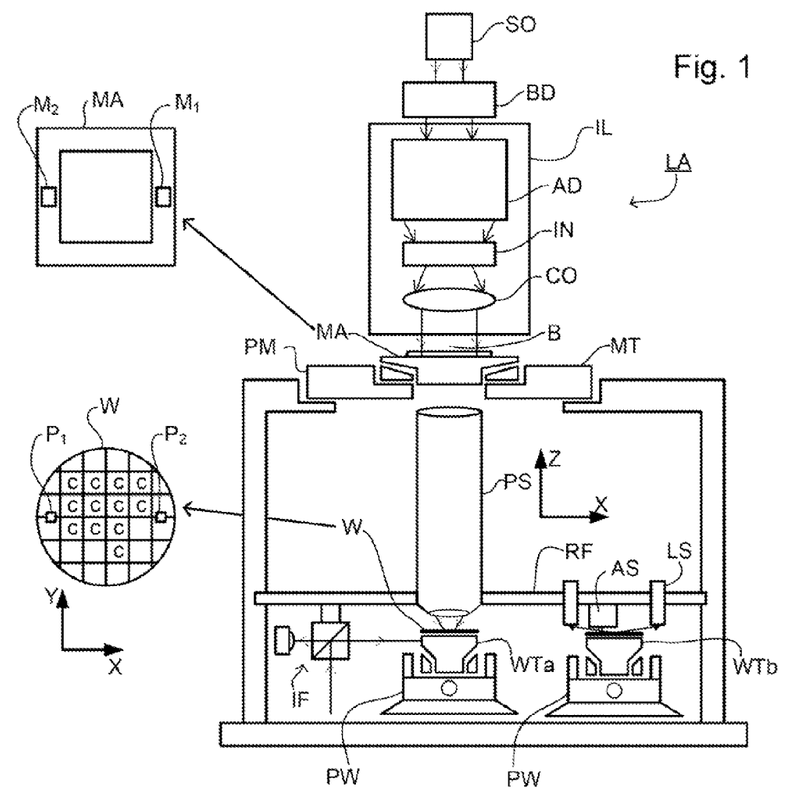
FIG. 1 depicts a lithographic apparatus according to an embodiment of the invention.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type such that at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan. In general, movement of the patterning device support (e.g., mask table) MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the patterning device support (e.g., mask table) MT may be connected to a short-stroke actuator only, or may be fixed.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. The alignment system, which detects the alignment markers is described further below.

The depicted apparatus could be used in at least one of the following modes:

1. In step mode, the patterning device support (e.g., mask table) MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WT are scanned synchronously while a pattern imparted to the radiation beam is projected onto a target portion C (i.e., a single dynamic exposure). The velocity and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has two substrate tables WTa, WTb and two stations—an exposure station and a measurement station—between which the substrate tables can be exchanged. While one substrate on one substrate table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS. This enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations.

Figure 2:
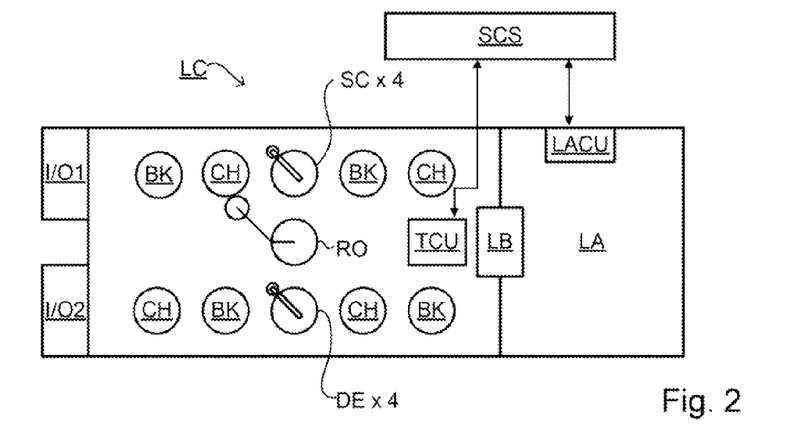
FIG. 2 depicts a lithographic cell or cluster according to an embodiment of the invention.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

Examples of dark field metrology can be found in international patent applications WO 2009/078708 and WO 2009/106279 which documents are hereby incorporated by reference in their entirety. Further developments of the technique have been described in patent publications US20110027704A and US20110043791A and in and in U.S. patent application Ser. No. 13/293,116, filed 9 Nov. 2011. The contents of all these applications are also incorporated herein by reference in their entireties.

Figures 3A, 3B, 3C, 3D:
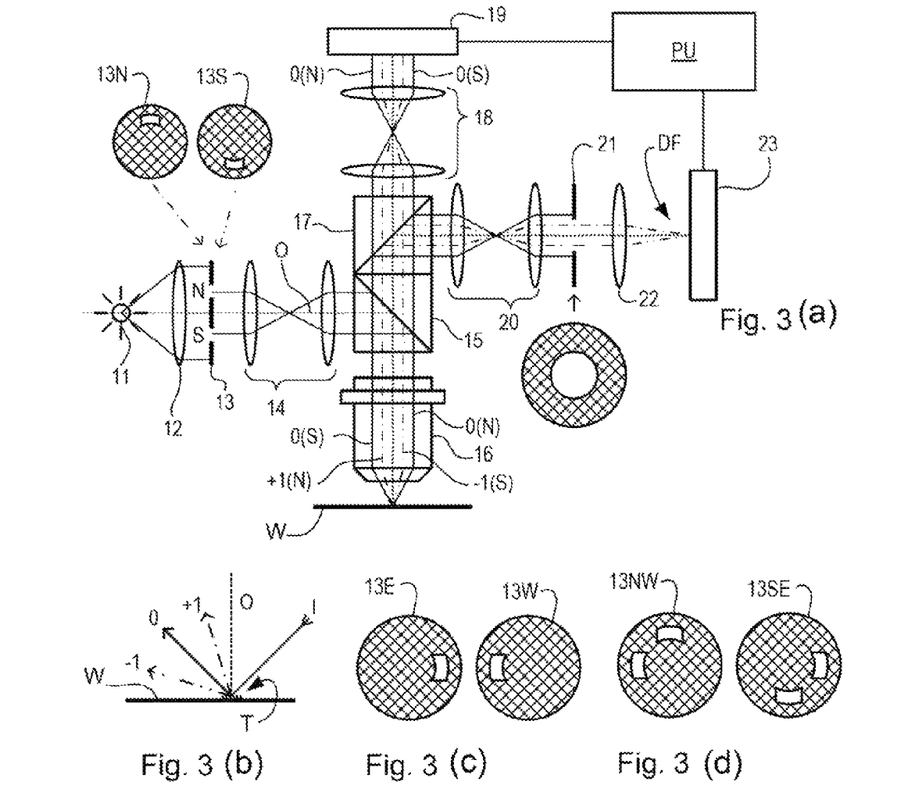
FIGS. 3A to 3D comprise (a) a schematic diagram of a dark field scatterometer for use in measuring targets according to embodiments of the invention using a first pair of illumination apertures, (b) a detail of diffraction spectrum of a target grating for a given direction of illumination (c) a second pair of illumination apertures providing further illumination modes in using the scatterometer for diffraction based overlay measurements and (d) a third pair of illumination apertures combining the first and second pair of apertures.

A dark field metrology apparatus suitable for use in embodiments of the invention is shown in FIG. 3(a). A target grating T and diffracted rays are illustrated in more detail in FIG. 3(b). The dark field metrology apparatus may be a stand-alone device or incorporated in either the lithographic apparatus LA, e.g., at the measurement station, or the lithographic cell LC. An optical axis, which has several branches throughout the apparatus, is represented by a dotted line 0. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

As shown in FIG. 3(b), target grating T is placed with substrate W normal to the optical axis O of objective lens 16. A ray of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches and illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g., a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction, which are not the subject of the present disclosure.

In the second measurement branch, optical system 20, 1 forms an image of the target on the substrate W on sensor 23 (e.g., a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to image processor and controller PU, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 3 are purely examples. In another embodiment of the invention, on-axis illumination of the targets is used and an aperture stop with an off-axis aperture is used to pass substantially only one first order of diffracted light to the sensor. In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Alternatively or in addition, a set of plates 13 could be provided and swapped, to achieve the same effect. A programmable illumination device such as a deformable mirror array or transmissive spatial sight modulator can be used also. Moving mirrors or prisms can be used as another way to adjust the illumination mode.

As just explained in relation to aperture plate 13, the selection of diffraction orders for imaging can alternatively be achieved by altering the pupil-stop 21, or by substituting a pupil-stop having a different pattern, or by replacing the fixed field stop with a programmable spatial light modulator. In that case the illumination side of the measurement optical system can remain constant, while it is the imaging side that has first and second modes. In the present disclosure, therefore, there are effectively three types of measurement method, each with its own advantages and disadvantages. In one method, the illumination mode is changed to measure the different orders. In another method, the imaging mode is changed. In a third method, the illumination and imaging modes remain unchanged, but the target is rotated through 180 degrees. In each case the desired effect is the same, namely to select first and second portions of the non-zero order diffracted radiation which are symmetrically opposite one another in the diffraction spectrum of the target. In principle, the desired selection of orders could be obtained by a combination of changing the illumination modes and the imaging modes simultaneously, but that is likely to bring disadvantages for no advantage, so it will not be discussed further.

While the optical system used for imaging in the present examples has a wide entrance pupil which is restricted by the field stop 21, in other embodiments or applications the entrance pupil size of the imaging system itself may be small enough to restrict to the desired order, and thus serve also as the field stop. Different aperture plates are shown in FIGS. 3(c) and (d) which can be used as described further below.

Typically, a target grating will be aligned with its grating lines running either north-south or east-west. That is to say, a grating will be aligned in the X direction or the Y direction of the substrate W. Note that aperture plate 13N or 13S can only be used to measure gratings oriented in one direction (X or Y depending on the set-up). For measurement of an orthogonal grating, rotation of the target through 90° and 270° might be implemented. More conveniently, however, illumination from east or west is provided in the illumination optics, using the aperture plate 13E or 13W, shown in FIG. 3(c). The aperture plates 13N to 13W can be separately formed and interchanged, or they may be a single aperture plate which can be rotated by 90, 180 or 270 degrees. As mentioned already, the off-axis apertures illustrated in FIG. 3(c) could be provided in field stop 21 instead of in illumination aperture plate 13. In that case, the illumination would be on axis.

FIG. 3(d) shows a third pair of aperture plates that can be used to combine the illumination modes of the first and second pairs. Aperture plate 13NW has apertures at north and east, while aperture plate 13SE has apertures at south and west. Provided that cross-talk between these different diffraction signals is not too great, measurements of both X and Y gratings can be performed without changing the illumination mode.

Figure 4:
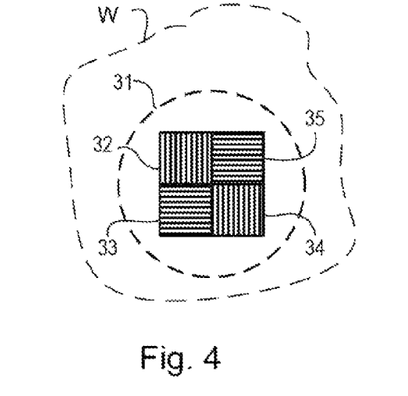
FIG. 4 depicts a form of multiple grating target and an outline of a measurement spot on a substrate.

FIG. 4 depicts a composite target formed on a substrate according to known practice. The composite target comprises four gratings 32 to 35 positioned closely together so that they will all be within a measurement spot 31 formed by the illumination beam of the metrology apparatus. The four targets thus are all simultaneously illuminated and simultaneously imaged on sensors 19 and 23. In an example dedicated to overlay measurement, gratings 32 to 35 are themselves composite gratings formed by overlying gratings that are patterned in different layers of the semi-conductor device formed on substrate W. Gratings 32 to 35 may have differently biased overlay offsets in order to facilitate measurement of overlay between the layers in which the different parts of the composite gratings are formed. Gratings 32 to 35 may also differ in their orientation, as shown, so as to diffract incoming radiation in X and Y directions. In one example, gratings 32 and 34 are X-direction gratings with biases of the +d, −d, respectively. This means that grating 32 has its overlying components arranged so that if they were both printed exactly at their nominal locations one of the components would be offset relative to the other by a distance d. Grating 34 has its components arranged so that if perfectly printed there would be an offset of d but in the opposite direction to the first grating and so on. Gratings 33 and 35 are Y-direction gratings with offsets +d and −d respectively. While four gratings are illustrated, another embodiment might require a larger matrix to obtain the desired accuracy. For example, a 3×3 array of nine composite gratings may have biases −4−d, −3d, −2d, −d, 0, +d, +2d, +3d, +4d. Separate images of these gratings can be identified in the image captured by sensor 23.

Figure 5:
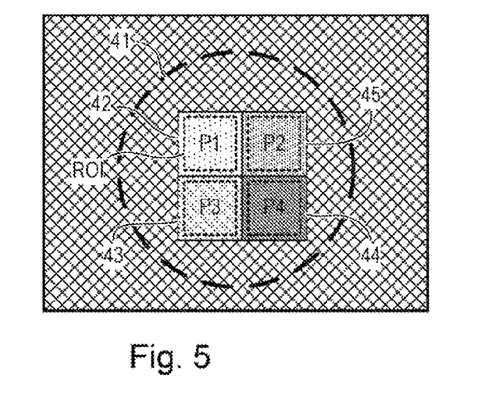
FIG. 5 depicts an image of the target of FIG. 4 obtained in the scatterometer of FIG. 3.

FIG. 5 shows an example of an image that may be formed on and detected by the sensor 23, using the target of FIG. 4 in the apparatus of FIG. 3, using the aperture plates 13NW or 13SE from FIG. 3(d). While the pupil plane image sensor 19 cannot resolve the different individual gratings 32 to 35, the image sensor 23 can do so. The dark rectangle represents the field of the image on the sensor, within which the illuminated spot 31 on the substrate is imaged into a corresponding circular area 41. Within this, rectangular areas 42-45 represent the images of the small target gratings 32 to 35. If the gratings are located in product areas, product features may also be visible in the periphery of this image field. Image processor and controller PU processes these images using pattern recognition to identify the separate images 42 to 45 of gratings 32 to 35. In this way, the images do not have to be aligned very precisely at a specific location within the sensor frame, which greatly improves throughput of the measuring apparatus as a whole. However the need for accurate alignment remains if the imaging process is subject to non-uniformities across the image field. In one embodiment of the invention, four positions P1 to P4 are identified and the gratings are aligned as much as possible with these known positions.

Once the separate images of the gratings have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an important example of such a parameter.

Figure 6:
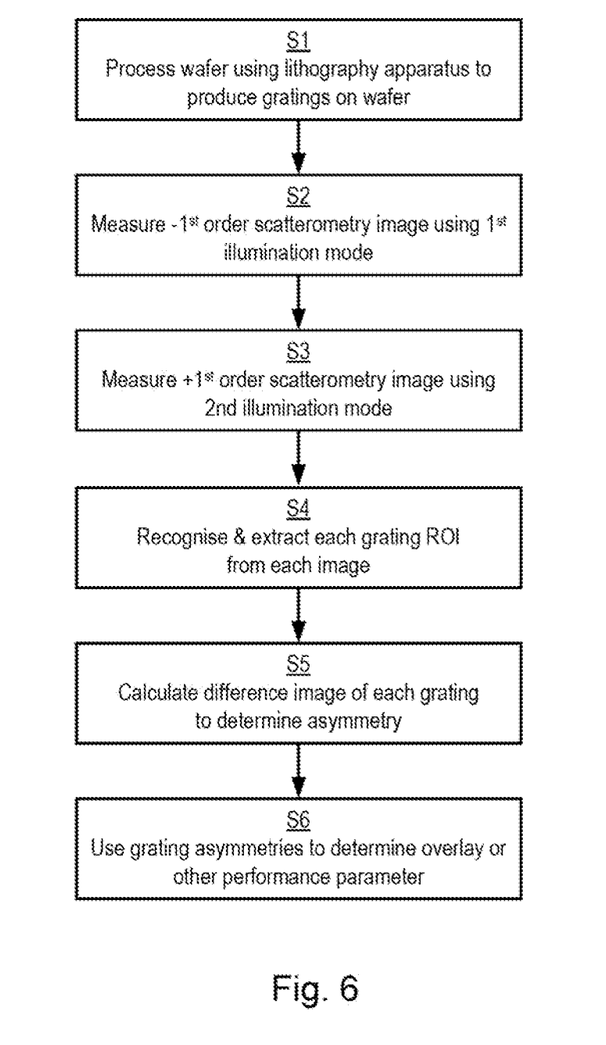
FIG. 6 is a flowchart showing the steps of an overlay measurement method using the scatterometer of FIG. 3 and adaptable to form an embodiment of the present invention.

FIG. 6 illustrates how, using for example the method described in application WO 2011/012624, overlay error between the two layers containing the component gratings 32 to 35 is measured through asymmetry of the gratings, as revealed by comparing their intensities in the +1 order and −1 order dark field images. At step S1, the substrate, for example a semiconductor wafer, is processed through the lithographic cell of FIG. 2 one or more times, to create a structure including the overlay targets 32-35. At S2, using the metrology apparatus of FIG. 3, an image of the gratings 32 to 35 is obtained using only one of the first order diffracted beams (say −1). Then, whether by changing the illumination mode, or changing the imaging mode, or by rotating substrate W by 180° in the field of view of the metrology apparatus, a second image of the gratings using the other first order diffracted beam (+1) can be obtained (step S3). Consequently the +1 diffracted radiation is captured in the second image.

Note that, by including only half of the first order diffracted radiation in each image, the 'images' referred to here are not conventional dark field microscopy images. The individual grating lines will not be resolved. Each grating will be represented simply by an area of a certain intensity level. In step S4, a region of interest (ROI) is carefully identified within the image of each component grating, from which intensity levels will be measured. This is done because, particularly around the edges of the individual grating images, intensity values can be highly dependent on process variables such as resist thickness, composition, line shape, as well as edge effects generally.

Having identified the ROI for each individual grating and measured its intensity, the asymmetry of the grating structure, and hence overlay error, can then be determined. This is done by the image processor and controller PU in step S5 comparing the intensity values obtained for +1 and −1 orders for each grating 32-35 to identify any difference in their intensity, and (S6) from knowledge of the overlay biases of the gratings to determine overlay error in the vicinity of the target T.

In the prior applications, mentioned above, various techniques are disclosed for improving the quality of overlay measurements using the basic method mentioned above. For example, the intensity differences between images may be attributable to differences in the optical paths used for the different measurements, and not purely asymmetry in the target. The illumination source 11 may be such that the intensity and/or phase of illumination spot 31 is not uniform. Corrections can the determined and applied to minimize such errors, by reference for example to the position of the target image in the image field of sensor 23. These techniques are explained in the prior applications, and will not be explained here in further detail. They may be used in combination with the techniques newly disclosed in the present application, which will now be described.

In the present application, we propose the use of three or more component gratings to measure overlay by the method of FIG. 6. By measuring asymmetries for gratings with at least three different biases, the calculations in step S6 can be modified so as to correct for feature asymmetry in the target gratings, such as is caused by bottom grating asymmetry in a practical lithographic process.

Figure 7:
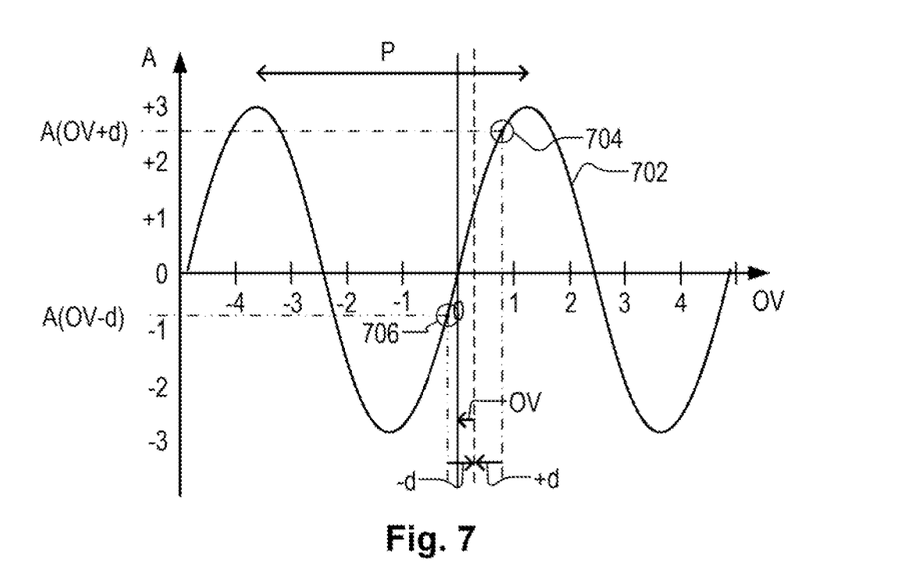
FIG. 7 illustrates principles of overlay measurement in an ideal target structure, not subject to feature asymmetry.

In FIG. 7 a curve 702 illustrates the relationship between overlay error OV and measured asymmetry A for an 'ideal' target having zero offset and no feature asymmetry within the individual gratings forming the overlay grating. These graphs are to illustrate the principles of the invention only, and in each graph, the units of measured asymmetry A and overlay error OV are arbitrary. Examples of actual dimensions will be given further below.

In the 'ideal' situation of FIG. 7, the curve 702 indicates that the measured asymmetry A has a sinusoidal relationship with the overlay. The period P of the sinusoidal variation corresponds to the period of the gratings. The sinusoidal form is pure in this example, but could include harmonics in other circumstances. For the sake of simplicity, it is assumed in this example (a) that only first order diffracted radiation from the targets reaches the image sensor 23 (or its equivalent in a given embodiment), and (b) that the experimental target design is such that within these first orders a pure sine-relation between intensity and overlay between top and bottom grating results. Whether this is true in practice is a function of the optical system design, the wavelength of the illuminating radiation and the pitch P of the grating, and the design and stack of the target. In an embodiment where 2nd, 3rd or higher orders also contribute to the intensities measured by sensor 23, or where the target design introduces harmonics in the first order, the skilled reader can readily adapt the teaching of the present application to allow for higher orders being present.

As mentioned above, biased gratings can be used to measure overlay, rather than relying on a single measurement. This bias has a known value defined in the patterning device (e.g., a reticle) from which it was made, that serves as an on-wafer calibration of the overlay corresponding to the measured signal. In the drawing, the calculation is illustrated graphically. In steps S1-S5, asymmetry measurements A(+d) and A(−d) are obtained for component gratings having biases +d and −d respectively. Fitting these measurements to the sinusoidal curve gives points 704 and 706 as shown. Knowing the biases, the true overlay error OV can be calculated. The pitch P of the sinusoidal curve is known from the design of the target. The vertical scale of the curve 702 is not known to start with, but is an unknown factor which we can call a 1st harmonic proportionality constant, K1. Using two measurements with of gratings with different, known biases one can solve two equations to calculate the unknowns K1 and overlay OV.

Figure 8:
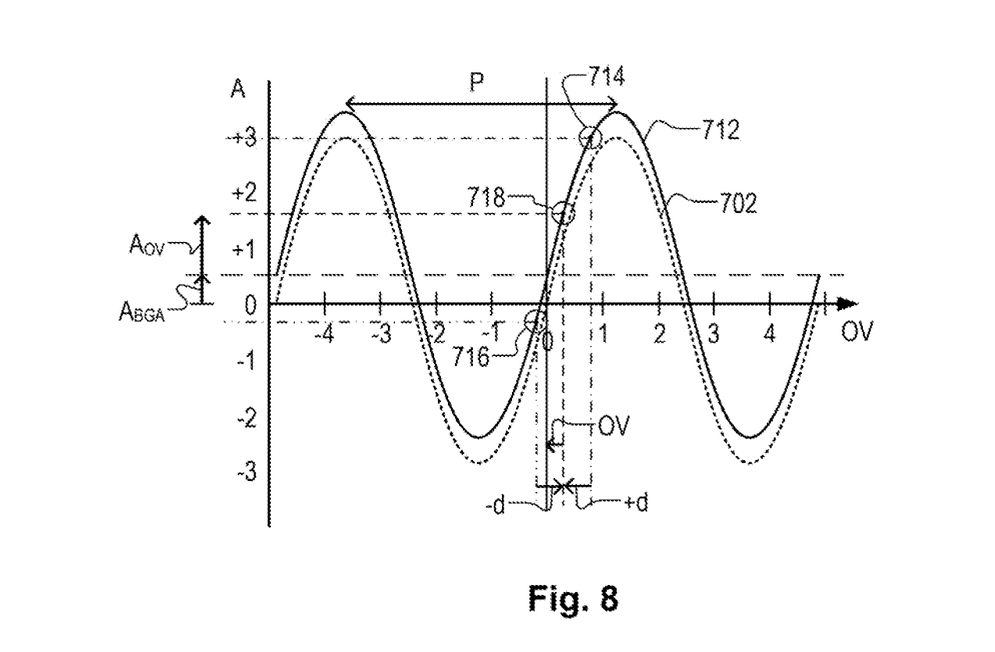
FIG. 8 illustrates novel principles of overlay measurement in a non-ideal target structure, with correction of feature asymmetry using an embodiment of the present invention.

FIG. 8 shows the effect of introducing feature asymmetry, for example by the effect of processing steps on the bottom grating layer. The 'ideal' sinusoidal curve 702 no longer applies. However, the inventors have recognized that, at least approximately, bottom grating asymmetry or other feature asymmetry has the effect of adding an offset to the asymmetry value A, which is relatively constant across all overlay values. The resulting curve is shown as 712 in the diagram, with label ABGA indicating the offset due to feature asymmetry. By providing multiple gratings with a biasing scheme having three or more different bias values, accurate overlay measurements can still be obtained by fitting the measurements to the off-set sine curve 712 and eliminating the constant.

Detailed examples of the modified measurement and calculations will be given below for various different biasing schemes. For a simple example to illustrate the principle, FIG. 8 shows three measurement points 714, 716 and 718 fitted to the curve 712. The points 714 and 716 are measured from gratings having bias +d and −d, the same as for the points 704 and 706 in FIG. 7. A third asymmetry measurement from a grating with zero bias (in this example) is plotted at 718. Fitting the curve to three points allows the constant asymmetry value ABGA that is due to feature asymmetry to be separated from the sinusoidal contribution AOV that is due to overlay error, so that the overlay error can be calculated more accurately.

As noted already, the overlay calculations of modified step S6 rely on certain assumptions. Firstly, it is assumed that 1st order intensity asymmetry due to the feature asymmetry (for example BGA) is independent of the overlay for the overlay range of interest, and as a result it can be described by a constant offset K0. The validity of this assumption has been tested in model-based simulations. Another assumption is that intensity asymmetry behaves as a sine function of the overlay, with the period P corresponding to the grating pitch. The number of harmonics can be designed to be small for the YS DBO case, because the small pitch-wavelength ratio only allows for a small number of propagating diffraction orders from the grating. Therefore, the overlay contribution to the intensity-asymmetry is assumed to be only sinusoidal with a 1st harmonic, and if necessary a 2nd harmonic.

FIG. 9 shows four example target designs (a) to (d), which can be used to implement overlay measurement with BGA correction, using the principles discussed above. To solve for the overlay, at least three gratings are required, because of the three unknowns: K0, K1, and overlay. The proposed composite target design can include three, but also for example four gratings. Each design (a) to (d) shows a proposed composite target layouts for performing the corrected overlay measurement in one direction. Each composite target layout comprises a plurality of component gratings, each forming one of the target structures referred to in the introduction and claims.

Each composite target (a) to (d) has component gratings with a basic dimension a transverse to the direction of periodicity and overall dimension 3a, 2a etc as shown. Hatching indicates the direction of the grating lines in the first grating of example (a) only. All the component gratings shown have grating lines in the same direction (e.g., X direction). A similar structure rotated by 90° would be provided to measure in the other (Y) direction, if desired, providing first and second groups of gratings. In an embodiment illustrated and described further below with references to FIG. 10, a composite grating target combining both X- and Y-direction gratings can be provided. Purely as examples for illustration, the first target (a) may have dimensions of a=4 µm or 5 µm, resulting in a total target size of 12×12 µm2 or 15×15 µm2. The second target (b) could have dimensions of the order of 16×16 µm2, while in target (c) the size is reduced to for example 16×8 µm2. The last target (d) may have dimensions of 10×10 µm2, for a 5×5 µm2 grating size (a=5 µm).

The bias-schemes are indicated in FIG. 9. Target (a) has three gratings with the biases +d, 0, −d, as discussed above with reference to FIG. 8. The bias schemes (b), (c) and (d) each have for four gratings with different permutations of bias value d and a sub-bias value Δd. The distinction between bias and sub-bias values is a matter of convenient notation. The biases for the four gratings can be rewritten as ±d1, ±d2, where ±d1=±(d−Δd), and ±d2=±(d+Δd).

The common property of these targets is that they can all be read out for overlay also with the dark-field image-based technique known from the previous patent applications mentioned above. This enables BGA-corrected overlay at small targets without stack-reconstruction. The calculations of modified step S6 will now be detailed for three examples, using the various targets illustrated.

Figure 9A:
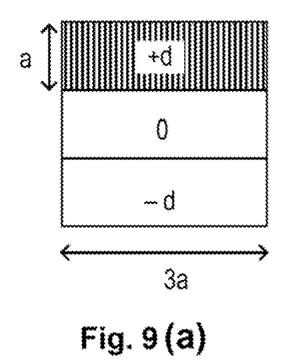
FIGS. 9A to 9D illustrate several composite grating structures (a) to (d) having bias schemes that can be used in embodiments of the present invention, for a single direction of overlay measurement.
Figure 9B:
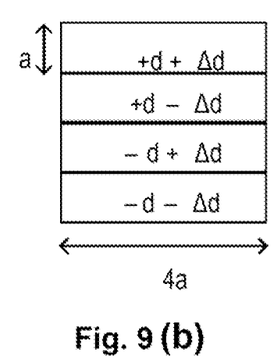
Figure 10:
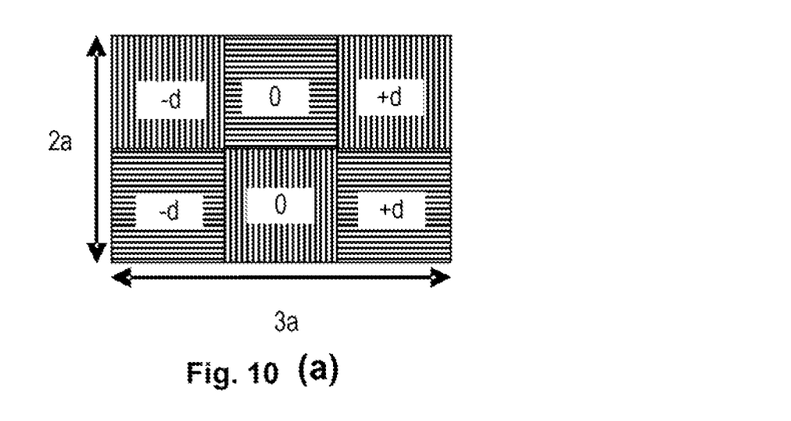
FIGS. 10A and 10B illustrate two composite grating structures (a) and (b) having bias schemes that can be used in embodiments of the present invention, combining component gratings for two orthogonal directions of overlay measurement.

FIG. 10 shows composite grating targets having (a) three and (b) four different biases, in which both X- and Y-direction gratings are provided in a single target area. The hatching indicates the directions of the grating lines. The bias schemes for each direction are the same as the ones in FIGS. 9 (*a*) and (*b*), but of course other schemes can be envisaged, provided that at least three different biases are included among the individual target structures. The X and Y gratings with each bias value are side-by-side, though that is not essential. The X and Y gratings are interspersed with one another in an alternating pattern, so that different X gratings are diagonally spaced, not side-by-side with one another, and Y gratings are diagonally spaced, not side-by-side with one another. This arrangement may help to reduce cross-talk between diffraction signals of the different biased gratings. The whole arrangement thus allows a compact target design, without good performance. While the component gratings in FIG. 10 are square, composite grating targets with X and Y component gratings can also be made with elongate gratings. Examples are described for example in published patent application US20120044470, which is incorporated by reference herein in its entirety.

Example 1

Solving for K0, K1, and ov with 3 gratings

Target (a) in FIG. 9 includes three component gratings with a symmetric bias scheme (−d, 0, and +d). To solve for the first harmonic and for a constant asymmetry signal coming from the bottom-grating asymmetry (BGA) we can write:

$$\Delta I_+ = K_0 + K_1 \cdot \sin(ov+d)$$

$$\Delta I_0 = K_0 + K_1 \cdot \sin(ov)$$

$$\Delta I_- = K_0 + K_1 \cdot \sin(ov-d)$$

where ΔI is the intensity difference representing the measured asymmetry and the suffix '+', '0' or '−' indicates the bias.

The solution of this set of equations can be written as:

$$ov = \mathrm{atan}\left\{\frac{[\Delta I_+ + \Delta I_- - 2\Delta I_0] \cdot \sin(d)}{[\Delta I_+ - \Delta I_-] \cdot (\cos(d) - 1)}\right\}$$

$$K_0 = \frac{\Delta I_+ + \Delta I_- - 2\Delta I_0 \cdot \cos(d)}{2 \cdot (1 - \cos(d))}$$

$$K_1 = \frac{[\Delta I_+ - \Delta I_-]}{2 \cdot \sin(d)} \cdot \sqrt{1 + \left(\frac{[\Delta I_+ + \Delta I_- - 2\Delta I_0] \cdot \sin(d)}{[\Delta I_+ - \Delta I_-] \cdot (\cos(d) - 1)}\right)^2}$$

This gives a direct calculation of the overlay, taking a constant asymmetry offset into account for the BGA or other feature asymmetry. We suggest to use a range of bias that is a significant proportion of the grating pitch P, to ensure that the curvature of the sine function is captured by the three sample points, and is distinguishable from noise that is inevitably present in the intensity measurements. A large bias range may be obtained for example by setting d=40 nm for a pitch P of 500 nm. The bias range of 2d is then 80 nm, representing more than 5% and in this case more than 10% but less than 20% of the pitch. However, if noise is not an issue, smaller bias-schemes may be chosen to enhance accuracy at a smaller overlay range. The bias should not be so big that the combination of bias and overlay error will push the total overlay into a different cycle of the sine function.

Example 2

Solving for K0, K1, and ov with 4 gratings

Figure 9C:
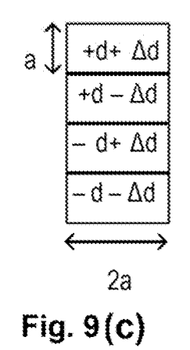
Figure 9D:
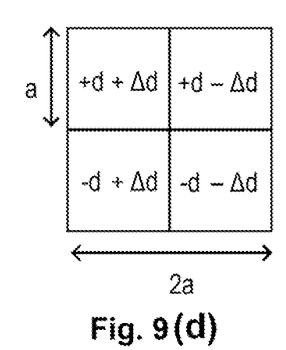

For the targets with four biased gratings, shown in FIGS. 9 (*b*), (c) and (d), the following equations can be written:

$$\Delta I_{-d-\Delta d} = K_0 + K_1 \cdot \sin(ov-d-\Delta d)$$

$$\Delta I_{-d+\Delta d} = K_0 + K_1 \cdot \sin(ov-d+\Delta d)$$

$$\Delta I_{+d-\Delta d} = K_0 + K_1 \cdot \sin(ov+d-\Delta d)$$

$$\Delta I_{+d+\Delta d} = K_0 + K_1 \cdot \sin(ov+d+\Delta d)$$

Solving for the unknown parameters yields:

$$ov = \operatorname{atan}\left\{\frac{((\Delta I_{-d+\Delta d} - \Delta I_{-d-\Delta d}) - (\Delta I_{+d+\Delta d} - \Delta I_{+d-\Delta d})) \cdot \sin(d-\Delta d)}{2 \cdot (\Delta I_{+d-\Delta d} - \Delta I_{-d+\Delta d}) \cdot \sin(d) \cdot \sin(\Delta d)}\right\}$$

$$K_0 = \frac{(\Delta I_{+d+\Delta d} + \Delta I_{-d-\Delta d}) \cdot \cos(d-\Delta d) - (\Delta I_{+d-\Delta d} + \Delta I_{-d+\Delta d}) \cdot \cos(d+\Delta d)}{2 \cdot (\cos(d+\Delta d) - \cos(d-\Delta d))}$$

$$K_1 = \frac{(\Delta I_{+d-\Delta d} - \Delta I_{-d+\Delta d})}{2 \cdot \sin(d-\Delta d)} \times \sqrt{1 + \left(\frac{((\Delta I_{-d+\Delta d} - \Delta I_{-d-\Delta d}) - (\Delta I_{+d+\Delta d} - \Delta I_{+d-\Delta d})) \cdot \sin(d-\Delta d)}{2 \cdot (\Delta I_{+d-\Delta d} - \Delta I_{-d+\Delta d}) \cdot \sin(d) \cdot \sin(\Delta d)}\right)^2}$$

Again, the range of biases should be significant as a proportion of the grating pitch P. For example it is suggested to use in this case a bias d=40 nm and a sub-bias $\Delta d$=20 nm, where the pitch P=500 nm. The biases thus range from +60 nm to −60 nm, that is a range of 120 nm overall. Here also, this is relatively large, representing more than 20% but less than 9% of the pitch, and will help to ensure that the sine behavior is observable above the intensity noise. Also here, if noise is not an issue, smaller bias-schemes may be chosen to enhance accuracy at a smaller overlay range. The bias should not be so big that the combination of bias and overlay error will push the total overlay into a different cycle of the sine function.

Example 3

Solving for K0, K1, K2, and ov with 4 gratings and 2nd harmonic

For the 4-gratings per target case above, also the second harmonic can be included if the design of the gratings and the optical system requires it. We can write:

$$\Delta I_{-d-\Delta d} = K_0 + K_1 \cdot \sin(ov - d - \Delta d) + K_2 \cdot \sin(2 \cdot (ov - d - \Delta d))$$

$$\Delta I_{-d+\Delta d} = K_0 + K_1 \cdot \sin(ov - d + \Delta d) + K_2 \cdot \sin(2 \cdot (ov - d + \Delta d))$$

$$\Delta I_{+d-\Delta d} = K_0 + K_1 \cdot \sin(ov + d - \Delta d) + K_2 \cdot \sin(2 \cdot (ov + d - \Delta d))$$

$$\Delta I_{+d+\Delta d} = K_0 + K_1 \cdot \sin(ov + d + \Delta d) + K_2 \cdot \sin(2 \cdot (ov + d + \Delta d))$$

To solve this set of equations we defining some new parameters as:

$$\Delta I_a = \Delta I_{+d+\Delta d} - \Delta I_{-d-\Delta d}$$

$$\Delta I_b = \Delta I_{+d-\Delta d} - \Delta I_{-d+\Delta d}$$

$$\Delta I_c = (\Delta I_{+d+\Delta d} - \Delta I_{+d-\Delta d}) - (\Delta I_{-d+\Delta d} - \Delta I_{-d-\Delta d})$$

where $$a_1 = 2 \cdot \sin(d + \Delta d)$$

$$a_2 = 2 \cdot \sin(2 \cdot (d + \Delta d))$$

$$b_1 = 2 \cdot \sin(d - \Delta d)$$

$$b_2 = 2 \cdot \sin(2 \cdot (d - \Delta d))$$

$$c_1 = -4 \cdot \sin(d) \cdot \sin(\Delta d)$$

$$c_2 = -4 \cdot \sin(2d) \cdot \sin(2\Delta d)$$

and $$z_0 = \frac{(a_1 b_2 - a_2 b_1) \cdot \Delta I_c}{c_1 \cdot (b_2 \Delta I_a - a_2 \Delta I_b)}$$

-continued $$z_1 = \frac{(2 \cdot b_1 c_2 - b_2 c_1) \cdot \Delta I_a + (a_2 c_1 - 2 \cdot a_1 c_2) \cdot \Delta I_b}{c_1 \cdot (b_2 \Delta I_a - a_2 \Delta I_b)}$$

$$Q = \frac{3 \cdot z_1 - z_0^2}{9}$$

$$R = \frac{2 \cdot z_0^2 - 9 \cdot z_0 \cdot (z_1 + 3)}{54}$$

$$D = Q^3 + R^2$$

$$S = \sqrt[3]{R + \sqrt{Q}}$$

$$T = \sqrt[3]{R - \sqrt{Q}}$$

The equations can then be solved, yielding three possible solutions:

$$ov_1 = \operatorname{atan}\left\{\frac{z_0}{3} + (S+T)\right\}$$

$$ov_2 = \operatorname{atan}\left\{\frac{z_0}{3} - \frac{1}{2}(S+T) + \frac{1}{2} \cdot i \cdot \sqrt{3}\,(S-T)\right\}$$

$$ov_3 = \operatorname{atan}\left\{\frac{z_0}{3} - \frac{1}{2}(S+T) - \frac{1}{2} \cdot i \cdot \sqrt{3}\,(S-T)\right\}$$

Of these results, the 3rd solution ov3 will usually be correct solution because the overlay in practice is normally small in comparison with the grating pitch.

As will be seen, any of these calculations will yield a BGA-corrected overlay measurement without the need for modeling the top & bottom gratings or any intervening layers such as BARC (antireflective coating). The examples work best with grating structures of which the ratio of pitch to wavelength is small, so that only a very limited number of higher diffraction orders are used in the measurements. Accurate results rely on distinguishing the constant offset due to BGA from a sine-like periodicity of known pitch, due to the overlay. The grating pitch and biasing schemes should therefore be designed so that the overlay should not produce a perfectly linear relation with the 1st order intensity differences $\Delta I$. The latter would be the case for macroscopic gratings that produce a triangular dependence on overlay. Generally, the desired sinusoidal relation will be obtained case for the small pitch-wavelength ratio usually employed in the apparatus and methods of FIGS. 3 to 6.

Furthermore, it is remarked that the technique disclosed here using three, four or more component gratings per overlay direction can be applied to large scatterometer targets, also referred to as standard targets, which are then modified to incorporate one or two additional biased gratings per overlay direction. Using the apparatus of FIG. 3, for example, the overlay in these larger targets can be measured by angle-resolved scatterometry using the pupil image sensor 19 instead of or in addition to measurements made in the dark-field imaging branch and sensor 23.

The targets in this proposal also allow for the standard overlay calculation methods that do not take the BGA into account ('linear'- and 'ATAN'-method), to be applied from the measurement.

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed.

In association with the physical grating structures of the targets as realized on substrates and patterning devices, an embodiment may include a computer program containing one or more sequences of machine-readable instructions describing a methods of producing targets on a substrate, measuring targets on a substrate and/or analyzing measurements to obtain information about a lithographic process. This computer program may be executed for example within unit PU in the apparatus of FIG. 3 and/or the control unit LACU of FIG. 2. There may also be provided a data storage medium (e.g., semiconductor memory, magnetic or optical disk) having such a computer program stored therein. Where an existing metrology apparatus, for example of the type shown in FIG. 3, is already in production and/or in use, the invention can be implemented by the provision of updated computer program products for causing a processor to perform the modified step S6 and so calculate overlay error with reduced sensitivity to feature asymmetry. The program may optionally be arranged to control the optical system, substrate support and the like to perform the steps S2-S5 for measurement of asymmetry on a suitable plurality of target structures.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 155, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method comprising:
    forming a set of targets on a substrate using a lithographic process, each target of the set of targets comprising an overlay bias, the overlay bias of each target of the set of targets being different from each other target of the set of targets;
    obtaining three or more asymmetry measurements from corresponding three or more targets of the set of targets, each of the three or more asymmetry measurements comprising:
        a first asymmetry value corresponding to an overlay error in the lithographic process, and
        a second asymmetry value corresponding to feature asymmetry in the set of targets; and
    calculating the overlay error based on the three or more asymmetry measurements and an assumed non-linear relationship between the overlay error and the three or more asymmetry measurements, such that the second asymmetry value corresponding to feature asymmetry is excluded from the calculated overlay error.

2. The method of claim 1, wherein the assumed non-linear relationship is a sinusoidal function or a combination of sinusoidal functions related harmonically to one another.

3. The method of claim 1, wherein the overlay error calculation is based on an assumption that the second asymmetry value corresponding, to feature asymmetry is constant for all values of overlay.

4. The method of claim 1, wherein the overlay error calculation is based on three asymmetry measurements.

5. The method of claim 1, wherein the overlay error calculation is based on four asymmetry measurements.

6. The method of claim 1, wherein:
    each target of the set of targets comprises periodic structures; and the overlay bias value is greater than about 5% or 10% or greater than about 15% or 20% of a pitch of the periodic structures.

7. The method of claim 1, wherein the three or more asymmetry measurements are obtained substantially in parallel.

8. The method of claim 1, wherein:
a first sub-set of the set of targets comprises a periodic structure having periodicity in a first direction;
a second sub-set of the set of targets comprises a periodic structure having periodicity in a second direction, the first and second directions being different from each other;
the overlay error calculation is performed separately in the first and second directions using both the first and second sub-sets; and
each target of the first and second sub-sets are arranged in an alternating pattern on the substrate to form a composite target so that the targets having periodicity in the first direction are separated from each other by targets having periodicity in the second direction.

9. An inspection apparatus comprising:
a support configured to hold a substrate having a set of targets, each of the targets comprising an overlay bias, the overlay bias of each of the targets being different from each other of the targets;
an optical system configured to detect radiation scattered by three or more targets of the set of targets to obtain corresponding three or more asymmetry measurements, each of the three or more asymmetry measurements comprising:
a first asymmetry value corresponding to an overlay error in the lithographic process, and
a second asymmetry value corresponding to feature asymmetry in the set of targets; and
a processor configured to calculate the overlay error based on the three or more asymmetry measurements and an assumed non-linear relationship between the overlay error and the three or more asymmetry measurements, such that the second asymmetry value corresponding to feature asymmetry is excluded from the calculated overlay error.

10. The apparatus of claim 9, wherein the assumed non-linear relationship is a sinusoidal function or a combination of sinusoidal functions related harmonically to one another.

11. The apparatus of claim 9, wherein the processor is configured to calculate the overlay error based on an assumption that the second asymmetry value corresponding to feature asymmetry is constant for all values of overlay.

12. The apparatus of claim 9, wherein the processor is configured to calculate the overlay error based on three asymmetry measurements.

13. The apparatus of claim 9, wherein the processor is configured to calculate the overlay error based on four asymmetry measurements for target structures having four different overlay bias values in the calculation of overlay error.

14. The apparatus of claim 9, wherein the optical system includes an image sensor and is configured to capture radiation scattered from the three or more targets substantially simultaneously on different portions of the image sensor.

15. A non-transitory computer readable medium having stored thereon computer-executable instructions that, in response to execution by a computing device, cause the computing device to perform operations comprising:
forming a set of targets on a substrate using a lithographic process, each target of the set of targets comprising an overlay bias, the overlay bias of each target of the set of targets being different from each other target of the set of targets;
obtaining three or more asymmetry measurements from corresponding three or more targets of the set of targets formed on the substrate, each of the three or more asymmetry measurements comprising:
a first asymmetry value corresponding to an overlay error in the lithographic process, and
a second asymmetry value corresponding to feature asymmetry in the set of targets; and
calculating the overlay error based on the three or more asymmetry measurements and an assumed non-linear relationship between the overlay error and the three or more asymmetry measurements, such that the second asymmetry value corresponding to feature asymmetry is excluded from the calculated overlay error.

16. A lithographic system comprising:
a lithographic apparatus comprising:
an illumination system configured to illuminate a pattern,
a projection system configured to project an image of the pattern onto a substrate, and
a support configured to hold a substrate having a set of targets, each of the targets comprising an overlay bias, the overlay bias of each of the targets being different from each other of the targets; and
an inspection apparatus comprising:
an optical system configured to detect radiation scattered by three or more targets of the set of targets to obtain corresponding three or more asymmetry measurements, each of the three or more asymmetry measurements comprising:
a first asymmetry value corresponding to an overlay error in the lithographic process, and
a second asymmetry value corresponding to feature asymmetry in the set of targets; and
a processor configured to calculate the overlay error based on the three or more asymmetry measurements an assumed non-linear relationship between the overlay error and the three or more asymmetry measurements, such that the second asymmetry value corresponding to feature asymmetry is excluded from the calculated overlay error,
wherein the lithographic apparatus is configured to use the calculated overlay error from the inspection apparatus in applying the pattern to further substrates.

17. A method comprising:
forming a set of targets on a substrate using a lithographic process, each target of the set of targets comprising an overlay bias, the overlay bias of each target of the set of targets being different from each other target of the set of targets;
obtaining three or more asymmetry measurements from corresponding three or more targets of the set of targets formed on the substrate, each of the three or more asymmetry measurements comprising:
a first asymmetry value corresponding to an overlay error in the lithographic process, and
a second asymmetry value corresponding to feature asymmetry in the set of targets; and
calculating the overlay error based on the three or more asymmetry measurements and an assumed non-linear relationship between the overlay error and the three or more asymmetry measurements, such that the second asymmetry value corresponding to feature asymmetry is excluded from the calculated overlay error; and
controlling the lithographic process for later substrates based on the calculated overlay error.

* * * * *

UNITED STATES PATENT AND TRADEMARK OFFICE
CERTIFICATE OF CORRECTION

PATENT NO. : 9,134,256 B2  Page 1 of 1
APPLICATION NO. : 13/799673
DATED : September 15, 2015
INVENTOR(S) : Smilde et al.

It is certified that error appears in the above-identified patent and that said Letters Patent is hereby corrected as shown below:

In The Claims

In column 20, line 59, claim 3, after "corresponding", please delete ",".
In column 22, line 35, claim 16, after "measurements", please add --and--.

Signed and Sealed this
Twenty-third Day of February, 2016

Michelle K. Lee
*Director of the United States Patent and Trademark Office*